United States Patent
Patankar et al.

(10) Patent No.: US 9,689,790 B2
(45) Date of Patent: Jun. 27, 2017

(54) ENVIRONMENTAL CONTROL SYSTEMS AND TECHNIQUES FOR MONITORING HEAT EXCHANGER FOULING

(71) Applicant: HONEYWELL INTERNATIONAL INC., Morristown, NJ (US)

(72) Inventors: Ravindra Patankar, Phoenix, AZ (US); Sunil Menon, Scottsdale, AZ (US); Emmanuel Obiesie Nwadiogbu, Scottsdale, AZ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 1015 days.

(21) Appl. No.: 13/930,568

(22) Filed: Jun. 28, 2013

(65) Prior Publication Data

US 2014/0008035 A1    Jan. 9, 2014

Related U.S. Application Data (60) Provisional application No. 61/668,399, filed on Jul. 5, 2012.

(51) Int. Cl.
*G06F 3/00* (2006.01)
*G01N 17/00* (2006.01)
(Continued)

(52) U.S. Cl.
CPC ........... *G01N 17/008* (2013.01); *F28F 27/00* (2013.01); *G05B 23/0221* (2013.01); *B64D 13/00* (2013.01)

(58) Field of Classification Search
USPC ........................................ 702/179, 183, 185
See application file for complete search history.

(56) References Cited

U.S. PATENT DOCUMENTS 5,590,706 A    1/1997    Tsou et al.
5,615,733 A    4/1997    Yang
(Continued)

FOREIGN PATENT DOCUMENTS

CN    101697078 A    4/2010

OTHER PUBLICATIONS

EP Exam Report for Application No. 13 174 813.9-1807 dated Jan. 17, 2014.

(Continued)

*Primary Examiner* — Lam Nguyen
(74) *Attorney, Agent, or Firm* — Lorenz & Kopf, LLP (57) ABSTRACT

Environmental control systems and techniques for monitoring heat exchanger fouling are provided herein. In an embodiment, a technique for monitoring heat exchanger fouling includes providing a correlation of heat exchanger fouling to an operating variable. The correlation is programmed into a maintenance system that includes a processor that is adapted to receive data regarding the operating variable. The operating variable is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof. Data regarding the operating variable is gathered via a sensor that is adapted to measure the operating variable. The measured operating variable is determined to correspond to excessive heat exchanger fouling in accordance with the correlation using the processor.

18 Claims, 4 Drawing Sheets

(51) Int. Cl.
G05B 23/02 (2006.01)
F28F 27/00 (2006.01)
B64D 13/00 (2006.01)

(56) References Cited

U.S. PATENT DOCUMENTS

| | | |
|---|---|---|
| 5,992,505 A | 11/1999 | Moon |
| 6,386,272 B1 | 5/2002 | Starner et al. |
| 8,199,313 B2 | 6/2012 | Okada |
| 8,762,106 B2 * | 6/2014 | Miller .................. G05B 17/02 702/179 |
| 2006/0225864 A1 | 10/2006 | Grieb et al. |
| 2008/0147365 A1 | 6/2008 | Parsad et al. |
| 2008/0183427 A1 | 7/2008 | Miller |
| 2009/0188645 A1 | 7/2009 | Harpster et al. |

OTHER PUBLICATIONS

EP Search Report for Application No. 13 174 813.9 dated Dec. 20, 2013.

* cited by examiner

ENVIRONMENTAL CONTROL SYSTEMS AND TECHNIQUES FOR MONITORING HEAT EXCHANGER FOULING

PRIORITY CLAIMS

This application claims the benefit of U.S. Provisional Application No. 61/668,399, filed Jul. 5, 2012.

TECHNICAL FIELD

The technical field generally relates to techniques for monitoring heat exchanger fouling and environmental control systems where the technique is implemented. More particular, the technical field relates to systems and techniques where readily available operating variables are employed for monitoring heat exchanger fouling.

BACKGROUND

Aircrafts are often operated in contaminant-prone environments, including in desert areas. The contaminant-prone environments, coupled with levels of maintenance that are practiced by particular airlines, often lead to accumulation and build-up of contamination on the narrowest passages of environmental control systems (ECSs), namely and often heat exchangers in the ECSs. Accumulated contamination may lead to reduction of performance over time, and in some cases may lead to failures that cause aircraft-on-ground (AOG), customer dissatisfaction, and elevated repair costs. Airframers and airlines in general prefer to avoid fixed maintenance cleaning intervals, instead preferring on-condition maintenance due to the high cost of removing and cleaning the ECSs at fixed intervals. In addition, on-wing cleaning is not often very practical.

Accumulation of contamination, also referred to as fouling, in heat exchangers of the ECSs has been investigated in the past. In particular, past investigations have focused upon causes of fouling and methods to avoid or mitigate such fouling. Other efforts have focused on detecting fouling in the heat exchangers of the ECSs, with appropriate steps taken to clean or provide notification of excessive fouling after detection. Conventional methods for detecting fouling in the heat exchangers of the ECSs include:
1. Examination of the heat transfer coefficient or heat conductance,
2. Simultaneous observations of pressure drops and mass flow rates,
3. Conducting temperature measurements,
4. Ultrasonic or electrical measurements,
5. Weighing of heat exchanger plates, and
6. Modeling the heat exchanger and comparing the prediction with filed data.

The conventional methods for detecting fouling all are prone to drawbacks. For example, to be sufficiently accurate, the conventional methods 1-3 require that the heat exchangers present successive steady states, i.e., the inlet temperatures and flows must be stable for a period long enough to be able to compute or measure the values of interest. Conventional method 4 is a local method limited to portions of the heat exchangers and cannot be generally applied to the heat exchangers as a whole. Conventional method 5 requires that the process be stopped, with the heat exchangers being disassembled for measurement. Such requirements are too restrictive or costly. Conventional method 6 is reliant upon the quality and fidelity of the mathematical modeling itself. For example, a Diagnostics, Prognostics and Health Management (DPHM) solution is known for aircraft ECS heat exchangers to detect on-line fouling by use of a dynamic non-linear mathematical model. The model parameters are a function of mass flow rates and core and fin temperatures. Measurements of the inlet and outlet temperatures and the mass flow rates are used for model parameter estimation with Extended Kalman Filtering (EKF). However, not all values that are employed in conventional mathematical modeling are available via measurements within conventional heat exchangers, and often require invasive sensing equipment. For example, mass flow rates and heat capacities are difficult to measure and require the invasive sensing equipment.

Accordingly, it is desirable develop new techniques for contamination monitoring of heat exchangers that could alert a maintenance crew in advance to prepare for a timely removal or cleaning of the heat exchangers and thereby minimize disruption when contamination levels exceed acceptable thresholds. Furthermore, other desirable features and characteristics of the present invention will become apparent from the subsequent detailed description of the invention and the appended claims, taken in conjunction with the accompanying drawings and this background of the invention.

BRIEF SUMMARY

Environmental control systems and techniques for monitoring heat exchanger fouling are provided herein. In an embodiment, a technique for monitoring heat exchanger fouling includes providing a correlation of heat exchanger fouling to an operating variable. The correlation is programmed into a maintenance system that includes a processor that is adapted to receive data regarding the operating variable. The operating variable is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof. Data regarding the operating variable is gathered via a sensor that is adapted to measure the operating variable. The measured operating variable is determined to correspond to excessive heat exchanger fouling in accordance with the correlation using the processor.

In another embodiment, a technique for predictive monitoring of a heat exchanger in an environmental control system that includes a controller, a maintenance system, and a fouling indicator is provided. The technique includes programming the maintenance system with a correlation of heat exchanger fouling to an operating variable. The maintenance system includes a processor that is adapted to receive data regarding the operating variable, and the operating variable is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof. Data regarding the operating variable is gathered from a sensor that is adapted to measure the operating variable via the controller, and the controller is in informational communication with the maintenance system. The measured operating variable is determined to correspond to excessive heat exchanger fouling in accordance with the correlation using the processor. An indication of excessive heat exchanger fouling is provided with the fouling indicator.

In another embodiment, an environmental control system (ECS) includes a sensor that is adapted to measure an operating variable of the environmental control system. The ECS includes an air conditioning machine that includes a heat exchanger. The air conditioning machine is adapted to transfer heat from a bleed flow that is provided by an engine of an aircraft to a ram flow that is provided from outside ambient air. The ECS further includes a maintenance system including a processor. A controller is in informational communication with the sensor and with the maintenance system. A fouling indicator is in informational communication with the maintenance system. The maintenance system is programmed with a correlation of heat exchanger fouling to the operating variable, and the operating variable is chosen from inlet temperatures of input streams into the heat exchanger and outlet temperatures of output streams out of the heat exchanger, heat exchanger pressure drop, overall heat transfer coefficient value, speed of rotation of the air conditioning machine that includes the heat exchanger, and combinations thereof.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Techniques for monitoring heat exchanger fouling and for predictive monitoring of environmental control system (ECS) heat exchangers are provided herein.

Figure 1:
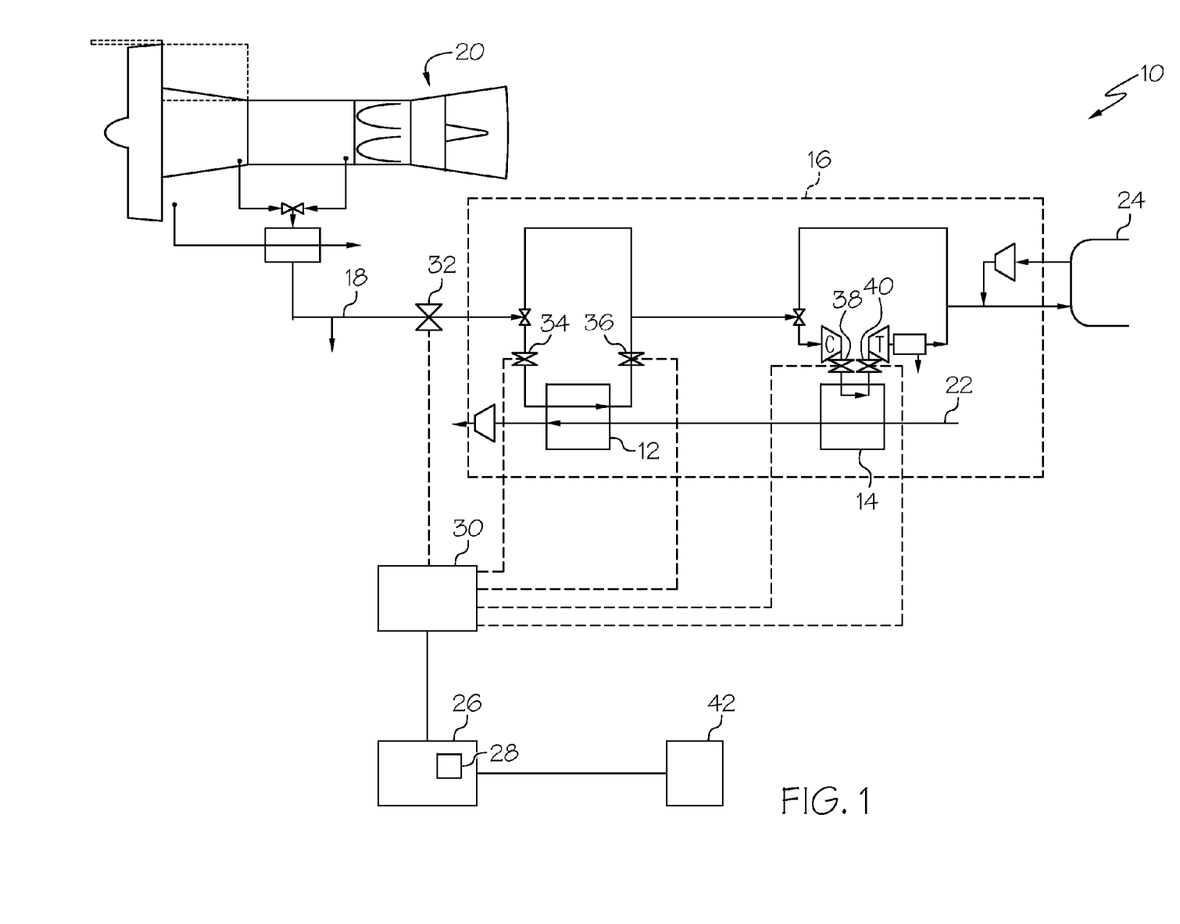
FIG. 1 is a schematic view of an aircraft environmental control system (ECS) including heat exchangers in accordance with an embodiment.

FIG. 1 generally illustrates an environmental control system (ECS) 10 of an aircraft including heat exchangers 12, 14, although it is to be appreciated that the techniques described herein are not limited to monitoring heat exchanger fouling in any particular type of system. The ECS 10 includes an air conditioning machine (ACM) 16 that is adapted to transfer of heat from a bleed flow 18 that is provided by an engine 20 of the aircraft to a ram flow 22 that is provided from outside ambient air for purposes of circulating air to a cabin 24 of the aircraft. The ACM 16 may include one or more heat exchangers 12, 14 and, in the embodiment shown in FIG. 1, includes two heat exchangers 12, 14. The ECS includes a maintenance system 26 that monitors heat exchanger fouling, among providing other functionality to the ECS 10, and the maintenance system 26 includes a processor 28 that provides feedback on heat exchanger fouling. A controller 30 may be in informational communication with sensors 32, 34, 36, 38, 40 in the ECS 10 for gathering data from one or more of the sensors 32, 34, 36, 38, 40, and the maintenance system 26 may be in informational communication with the controller 30 for receiving the data gathered by the controller 30. A fouling indicator 42 may be in informational communication with the maintenance system 26 for providing an indication of excessive heat exchanger fouling. The fouling indicator 42 may provide the indication of excessive heat exchanger fouling through any signaling mechanism including, but not limited to, an audio signal, a visual signal, or electronic display readout.

In accordance with the techniques described herein, a correlation of heat exchanger fouling to an operating variable is provided. More specifically, the correlation is programmed into the maintenance system 26, with the processor 28 of the maintenance system adapted to receive data regarding the operating variables) at issue and further adapted to execute the correlation. The data may be gathered via an embedded sensor or sensors 32, 34, 36, 38, 40, such as existing sensors in ECSs or new embedded sensors that are incorporated into the ECSs for purposes of gathering the desired data. The sensors as shown in FIG. 1 include a pressure sensor 32, an inlet temperature sensor 34 and an outlet temperature sensor 36 for the bleed flow 18 into and out of the first heat exchanger 12, and an inlet temperature sensor 38 and an outlet temperature sensor 40 for the bleed flow 18 into and out of the second heat exchanger 14. It is to be appreciated that positioning and configuration of the sensors 32, 34, 36, 38, 40 as shown in FIG. 1 is only representative, and additional sensors may be present that are not shown. In an embodiment, the data from the embedded sensors 32, 34, 36, 38, 40 is gathered via the controller 30 and provided to the maintenance system 26 for analysis and decision. In an embodiment, the correlation that is programmed into the maintenance system relies only upon data that is provided from existing pressure sensors and/or temperature sensors that are included in the ECS. In various embodiments, the operating variable upon which the correlation relies is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof. Such operating variables are generally available with embedded sensors of existing ECSs.

In an embodiment, mathematical models may be employed within the correlations that are programmed into the maintenance system, although in other embodiments it is to be appreciated that a direct correlation of heat exchanger fouling to the operating variable may be established without reliance on mathematical models. In an embodiment, a mathematical model that uses heat exchanger effectiveness is provided to relate heat exchanger fouling to heat exchanger effectiveness. In order to define the effectiveness of a heat exchanger, a maximum possible heat transfer that can be hypothetically achieved in a counter-flow heat exchanger of infinite length is first determined. To explain, one fluid will experience the maximum possible temperature difference, which is the temperature difference between the inlet temperature ($T_{h,i}$) of a hot stream (e.g., the bleed stream 18) and the inlet temperature ($T_{c,i}$) of a cold stream (e.g., the ram flow 22). Determination of effectiveness proceeds by calculating the heat capacity rates (i.e. mass flow rate multiplied by specific heat) for hot fluids ($C_h$) in the hot stream and cold fluids ($C_c$) in the cold stream, respectively, and denoting the smaller one (min($C_c$,$C_h$)) as $C_{min}$. The reason for selecting the smaller heat capacity rate is to include the maximum feasible heat transfer among the working fluids, determined by the slowest heat transferring fluid. A quantity:

$$q_{max} = C_{min}(T_{h,i} - T_{c,i}) \quad (1)$$

is then found, where $q_{max}$ is the maximum heat that could be transferred between the fluids. According to the above equation (1), to experience the maximum heat transfer, the heat capacity should be minimized since the maximum possible temperature difference is employed. This justifies the use of $C_{min}$ in the equation.

Effectiveness (E), is a ratio between the actual heat transfer rate and the maximum possible heat transfer rate:

$$E = q/q_{max} \quad (2)$$

where:

$$q = C_h \cdot (T_{h,i} - T_{h,o}) = C_c \cdot (T_{c,o} - T_{c,i}) \quad (3)$$

where $T_{h,o}$, $T_{c,o}$ are the outlet temperatures of the hot side and cold side, respectively. Effectiveness (E) is a dimensionless quantity between 0 and 1. Equation (3) above can be rewritten as:

$$q = \min(C_c, C_h) \cdot \max(T_{h,i} - T_{h,o}, T_{c,o} - T_{c,i}) \quad (4)$$

Using equations (1), (2), and (4), the following equation (5) is derived:

$$E = \frac{\max(T_{h,i} - T_{h,o}, T_{c,o} - T_{c,i})}{T_{h,i} - T_{c,i}} \quad (5)$$

The mathematical model derived in equation (5) for heat exchanger effectiveness relies upon temperatures alone, which are generally easier to measure than other quantities in equations (1), (2), and (3).

Figure 2:
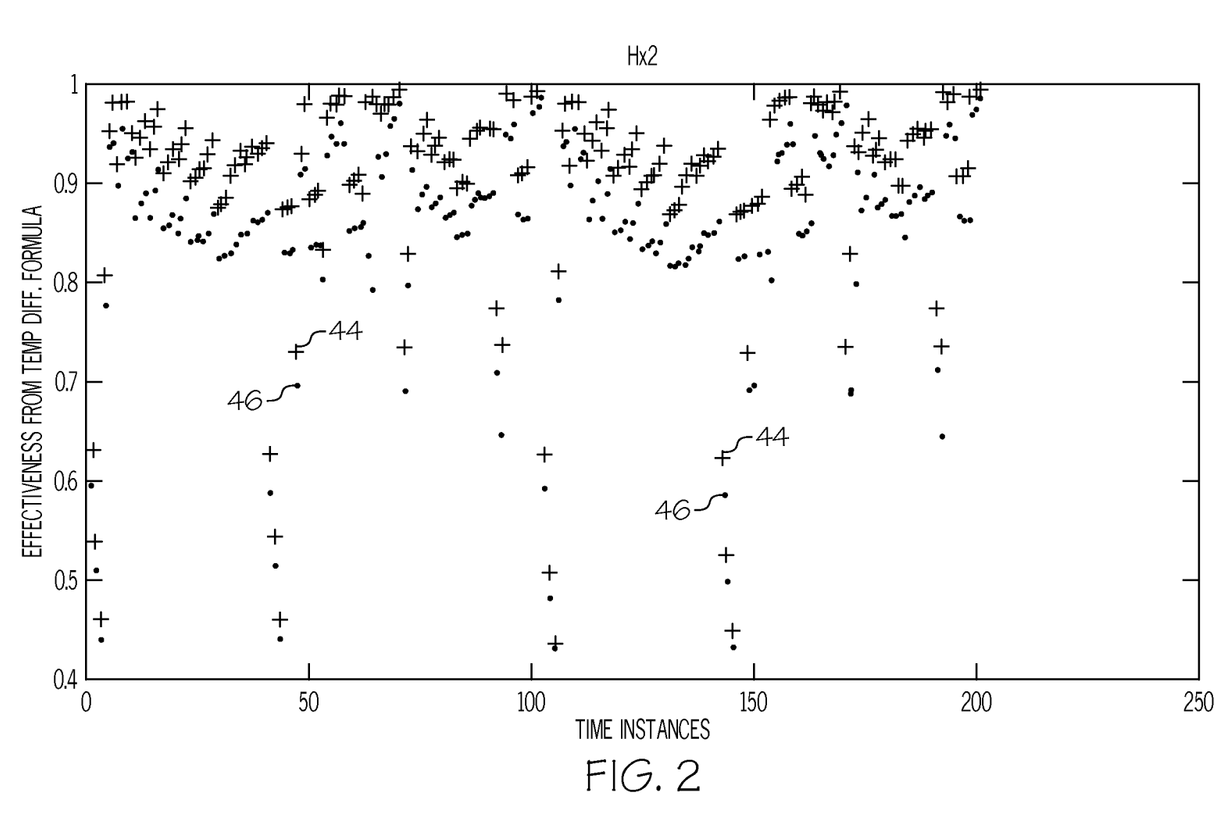
FIG. 2 is a graph illustrating heat exchanger effectiveness under various operating conditions (x-axis) and under original (designated by circles) and fouled (degraded, designated by crosses) conditions.

In accordance with the techniques described herein, a determination is made as to whether the measured operating variable corresponds to excessive heat exchanger fouling. Excessive heat exchanger fouling, as referred to herein, represents a degree of fouling that is pre-determined to require action in response to the heat exchanger fouling (e.g., replacement, cleaning, inspection or other attention that could be initiated by the fouling indicator 42). The determination may be made in accordance with the correlation that is programmed into the maintenance system 26, using the processor. For example, in an embodiment where the mathematical model that uses heat exchanger effectiveness is provided to relate heat exchanger fouling to heat exchanger effectiveness, FIG. 2 shows the heat exchanger effectiveness computed from equation (5) for an original condition heat exchanger and a degraded (fouled) heat exchanger, with the plus signs 44 representing values for heat exchanger effectiveness for original condition heat exchangers and with dots 46 representing heat exchanger effectiveness for degraded heat exchangers. In particular, the original condition heat exchanger may represent a heat exchanger prior to use, while the degraded heat exchanger represents the same heat exchanger at the time that the measurements are taken. The difference in effectiveness under the two conditions provides a clear indication of fouling and may be employed to render a determination of whether the heat exchanger is excessively fouled. It is to be appreciated that FIG. 2 is illustrative of effectiveness differences between original condition heat exchangers and corresponding degraded heat exchangers, and that specific differences between effectiveness for original condition heat exchangers and corresponding degraded heat exchangers that warrant service may be established based upon particular applications. Differences in effectiveness for the heat exchanger may be tracked over time to render a determination regarding excessive fouling. A cumulative sum (CUSUM) test can be performed to detect fouling in the heat exchanger over time. A CUSUM control chart is a type of time-weighted control chart that displays the CUSUMs of the deviations of each sample from the target value. Because it is cumulative, even minor drifting in the process mean will lead to steadily increasing cumulative deviation values. The CUMSUM control chart is useful in detecting difference in effectiveness values that are slowly deviating from target values due to contamination. If a trend develops, it may be taken as evidence that the contamination has built-up. As an example, w threshold level of 15-20% of the clean effectiveness value can be specified and a warning can be sent to the maintenance crew that the heat exchanger needs attention. Alternatively, a determination on excessive fouling may be made based on a single measurement of difference in effectiveness. For example, in an embodiment, a calculated difference in effectiveness of at least about 0.1, such as from about 0.1 to about 0.5, or such as from about 0.2 to about 0.3, may represent a determination that the degraded heat exchanger should be serviced.

In another embodiment, when the inlet temperatures of the hot stream and the cold stream into the heat exchanger and the outlet temperatures of the hot stream and cold stream out of the heat exchanger for both a hot side and a cold side are known, those temperature values are gathered and a mathematical model that uses Log Mean Temperature Difference (LMTD) is provided to relate heat exchanger fouling to the LMTD. LMTD can be calculated and used as an inverse proxy for the heat exchanger effectiveness. For a counter flow heat exchanger, LMTD can be calculated in accordance with equation (6):

$$LMTD = \frac{(T_{h,i} - T_{c,o}) - (T_{h,o} - T_{c,i})}{\ln \frac{(T_{h,i} - T_{c,o})}{(T_{h,o} - T_{c,i})}} \quad (6)$$

Figure 3:
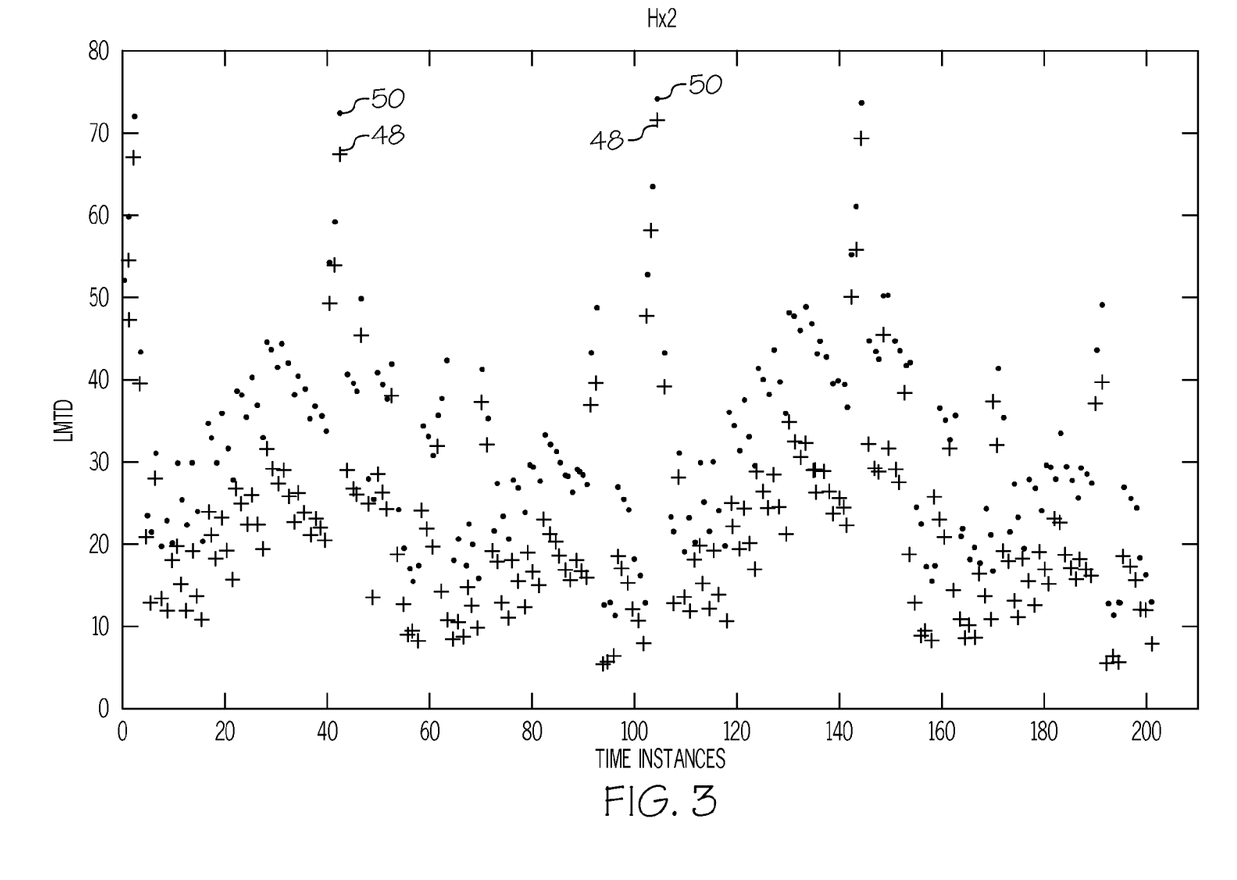
FIG. 3 is a graph of log mean temperature difference plotted for the same data for which effectiveness is plotted in FIG. 2, which is taken at different time instances (x-axis) and under original (designated by circles) and fouled (degraded, designated by crosses) conditions.

The LMTD computed from equation (6) is plotted in FIG. 3 for the same data for which effectiveness was plotted in FIG. 2, with plus signs 48 representing LMTD for original condition heat exchangers and with circles 50 representing LMTD for degraded heat exchangers. The rise in LMTD can be used as an indicator of the heat exchanger fouling. In particular, the original condition heat exchanger may represent a heat exchanger prior to use, while the degraded heat exchanger represents the same heat exchanger at the time that the measurements are taken. The difference in LMTD under the two conditions provides a clear indication of fouling and may be employed to render a determination of whether the heat exchanger is excessively fouled in the same manner as described above. It is to be appreciated that FIG. 3 is illustrative of LMTD differences between original condition heat exchangers and corresponding degraded heat exchangers, and that specific differences between LMTD for original condition heat exchangers and corresponding degraded heat exchangers that warrant service may be established based upon particular applications. For example, in an embodiment, a calculated difference in LMTD of at least about 1, such as from about 1 to about 10, or such as from about 2 to about 5, may represent a determination that the degraded heat exchanger should be serviced.

In another embodiment of a technique, heat exchanger pressure drop is employed for determining fouling. In particular, a correlation of heat exchanger fouling to heat exchanger pressure drop is provided and programmed into the maintenance system. This technique is applicable when pressure sensor(s) are provided that are adapted to directly measure pressure drop within the heat exchanger, which may include directly measuring pressure drop within the ECS. External contamination on the core of the heat exchanger will be difficult to measure in an open system. However, for internal heat exchanger core and passages, this approach is feasible. To employ embodiments of this technique, it may be necessary to modify existing ECSs to include additional pressure sensors (not shown), which add cost and weight.

Figure 4:
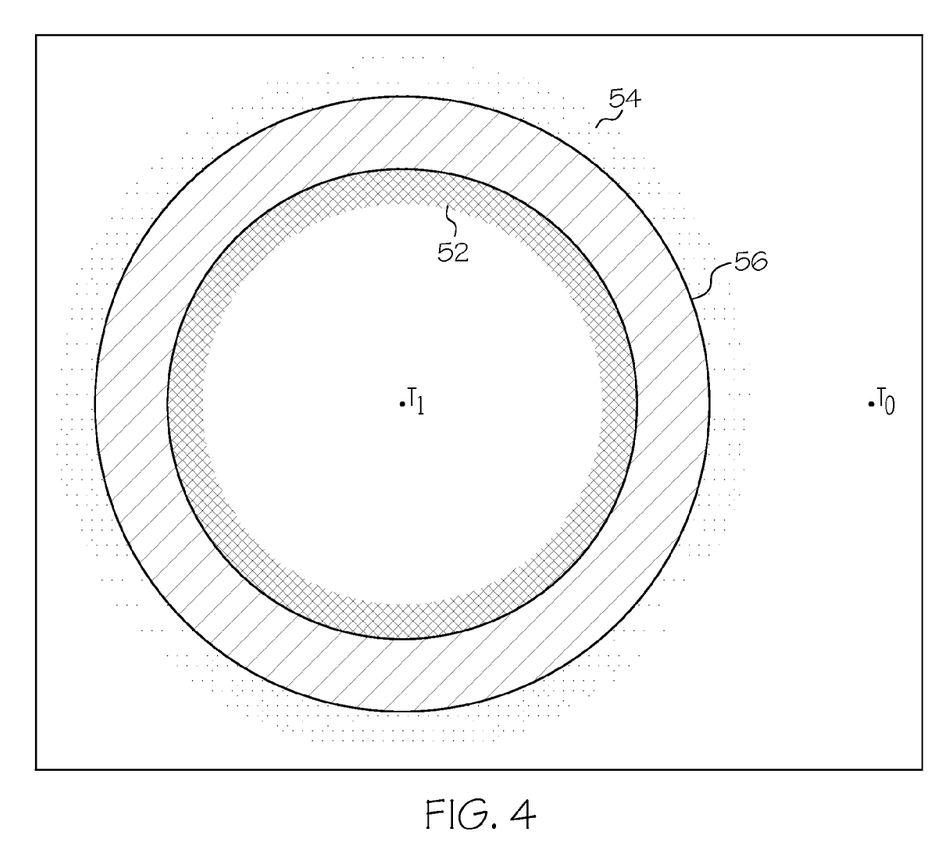
FIG. 4 is a schematic cross-sectional view of a duct of a heat exchanger illustrating a fouling effect in the duct.

In another embodiment of a technique, a mathematical model that uses heat exchanger heat exchanger number of transfer units (NTUs) is provided to relate heat exchanger fouling to the heat exchanger NTUs. In the technique of this embodiment, existing sensors in a typical ECU are used to determine real time overall heat transfer coefficient value (UA) of the heat exchanger. Referring to FIG. 4, contamination/fouling is shown both inside 52 and outside 54 a generic duct passage 56 of a heat exchanger. The UA value is used to analyze heat transfer contamination fouling of heat exchangers. It includes the effect of hot and cold side convection, conduction, and fouling resistance ($R_f$) of a heat exchanger, with fouling resistance ($R_f$) represented by equation (7):

$$R_f = 1/U_{actual} - 1/U_{clean} \quad (7)$$

The general equation (8) below shows the relationship between UA value, thermal resistances such as conduction and fouling resistance ($R_f$):

$$\frac{1}{UA} = \sum \frac{1}{hA} + \sum R \quad (8)$$

A is a heat exchanger total outer heat transfer area. UA value can be determined via the NTU formula of equation (9), using the heat capacity rate (C) of the bleed flow (which is also referred to above as the hot stream):

$$NTU = UA/C_{bleed} \quad (9)$$

Equation (9) is correct if the bleed flow into the heat exchanger is the minimum capacity rate fluid, which it generally is. However, in some cases like cruise, the ram flow (which is also referred to above as the cold stream) may be reduced so that the cold side capacity rate may be lower. If both the bleed mass flow rate and the ram mass flow rate can be estimated from onboard data (bleed mass flow rate should be available and ram mass flow rate may be estimated from ACM speed or ram door position and flight conditions, determined during flight testing), then equation (9) would use the definition of $NTU = UA/C_{min}$, where $C_{min} = MIN(m_c \cdot c_h, m_h \cdot c_h)$.

For a Cross flow (single pass) heat exchanger such the one used typically in air conditioning systems (both fluids unmixed), equation (10) is a curve fit for the series solution for cross flow heat exchangers. Performance codes for cross flow heat exchangers use series solution rather than the curve fit so the accuracy is improved at higher NTU values. This series could also be used above NTU values greater than about 7 for improved accuracy. With a computer program, the more exact series solution technique for cross flow heat exchangers can be programmed $$E = 1 - \exp\left(\left(\frac{C_{ram}}{C_{bleed}}\right)(NTU) ** 0.22 \cdot B\right) \quad (10)$$

$$B = \{\exp - \left(\frac{C_{bleed}}{C_{ram}}\right)(NTU) ** 0.78\} - 1\}$$

In the procedure in accordance with the mathematical model of equation (10), it can be seen that the effectiveness of the heat exchanger (E) is a direct function of the NTU and, hence, the contamination fouling as reflected in the overall heat loss coefficient U. Thus, NTU can be employed through various mathematical models to relate to heat exchanger fouling.

The mass flow through the heat exchanger can be determined via the speed of rotation of the ACM that includes the heat exchanger based on a speed sensor installed and the use the fan laws according to equation (11):

$$m_2 = m_1 \cdot \frac{rpm_1}{rpm_2} \quad (11)$$

Bleed temperatures can use existing temperature sensors upstream and downstream of the heat exchangers. Ram inlet temperature can be provided from ambient air temperature (aircraft sensor) with an appropriate correction for heat transfer from adjacent structures inside the ram channel.

In an embodiment, where heat exchanger fouling is to be monitored over a range of operating conditions, e.g., with a range of differences between minimum and maximum heat capacity rates during operation of the heat exchanger, the mathematical model that uses heat exchanger heat exchanger number of transfer units (NTUs) may be used instead of the mathematical model that uses heat exchanger effectiveness. In particular, change in NTU is more consistent over the various operating conditions than heat exchanger effectiveness, which may render determination of excessive heat exchanger fouling easier over the range of operating conditions.

To render a determination that the heat exchanger is excessively fouled, a cumulative sum (CUSUM) test can be performed to detect fouling in the heat exchanger over time in the same manner as described above. Alternatively, a single measurement may be employed to render the determination. After rendering the determination that heat exchanger is excessively fouled, the maintenance system may provide a signal to the fouling indicator, where a system user may be notified of the excessive fouling.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A technique for monitoring heat exchanger fouling, wherein the technique comprises the steps of:
providing a correlation of heat exchanger fouling to an operating variable, wherein the correlation is programmed into a maintenance system that includes a processor adapted to receive data regarding the operating variable, wherein the operating variable is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof, and wherein providing the correlation comprises providing a mathematical model that uses heat exchanger effectiveness to relate heat exchanger fouling to the heat exchanger effectiveness;
gathering data regarding the operating variable via a sensor that is adapted to measure the operating variable; and
determining that the measured operating variable corresponds to excessive heat exchanger fouling in accordance with the correlation using the processor.

2. The technique of claim 1, wherein the maintenance system is an existing maintenance system, and wherein providing the correlation comprises programming the existing maintenance system with the correlation.

3. The technique of claim 1, wherein the heat exchanger is a component of an environmental control system that includes the maintenance system.

4. The technique of claim 3, wherein gathering the data comprises gathering the data via existing embedded sensors in the environmental control system.

5. The technique of claim 1, wherein providing the mathematical model that uses the heat exchanger effectiveness comprises providing the mathematical model relying on temperatures alone.

6. The technique of claim 1, wherein determining that the measured operating variable corresponds to excessive heat exchanger fouling comprises calculating a difference in effectiveness between an original condition heat exchanger and a degraded heat exchanger.

7. The technique of claim 6, wherein determining that the measured operating variable corresponds to excessive heat exchanger fouling further comprises determining that the calculated difference in effectiveness between the original condition heat exchanger and the degraded heat exchanger is different by at least about 0.1.

8. The technique of claim 1, wherein gathering data regarding the operating variable comprises gathering inlet temperatures of input streams into the heat exchanger and outlet temperatures of output streams out of the heat exchanger on both a hot side and a cold side of the heat exchanger.

9. The technique of claim 8, wherein providing the correlation further comprises providing a mathematical model that uses Log Mean Temperature Difference between an original condition heat exchanger and a degraded heat exchanger to relate heat exchanger fouling to the Log Mean Temperature Difference.

10. The technique of claim 9, wherein determining that the measured operating variable corresponds to excessive heat exchanger fouling comprises determining that the calculated difference in Log Mean Temperature Difference between the original condition heat exchanger and the degraded heat exchanger is different by at least about 1.

11. The technique of claim 1, wherein providing the correlation of heat exchanger fouling to the operating variable further comprises providing the correlation of heat exchanger fouling to heat exchanger pressure drop.

12. The technique of claim 11, wherein the sensor is a pressure sensor adapted to directly measure pressure drop within the heat exchanger, and wherein gathering data regarding the operating variable comprises gathering pressure measurements with the pressure sensor.

13. The technique of claim 1, wherein providing the correlation further comprises providing a mathematical model that uses heat exchanger number of transfer units to relate heat exchanger fouling to the heat exchanger number of transfer units.

14. The technique of claim 13, wherein providing the mathematical mode that uses the heat exchanger number of transfer units comprises providing the mathematical model relying upon overall heat transfer coefficient value of the heat exchanger.

15. The technique of claim 14, wherein providing the mathematical mode that uses the heat exchanger number of transfer units comprises providing the mathematical model where heat exchanger effectiveness is a direct function of the heat exchanger number of transfer units.

16. The technique of claim 14, wherein heat exchanger fouling is monitored over a range of differences between minimum and maximum heat capacity rates during operation of the heat exchanger.

17. A technique for predictive monitoring of a heat exchanger in an environmental control system comprising a controller, a maintenance system, and a fouling indicator, wherein the technique comprises the steps of:
programming the maintenance system with a correlation of heat exchanger fouling to an operating variable, wherein the correlation is programmed into the maintenance system that includes a processor adapted to receive data regarding the operating variable, wherein the operating variable is chosen from inlet temperatures of input streams into the heat exchanger and outlet temperatures of output streams out of the heat exchanger, heat exchanger pressure drop, overall heat transfer coefficient value, speed of rotation of an air conditioning machine that includes the heat exchanger, and combinations thereof, and wherein providing the correlation comprises providing a mathematical model that uses heat exchanger effectiveness to relate heat exchanger fouling to the heat exchanger effectiveness;
gathering data regarding the operating variable from a sensor that is adapted to measure the operating variable via the controller, wherein the controller is in informational communication with the maintenance system;
determining that the measured operating variable corresponds to excessive heat exchanger fouling in accordance with the correlation using the processor; and
providing an indication of excessive heat exchanger fouling with the fouling indicator.

18. An environmental control system comprising:
a sensor adapted to measure an operating variable of the environmental control system;
an air conditioning machine comprising a heat exchanger, wherein the air conditioning machine is adapted to transfer heat from a bleed flow that is provided by an engine of an aircraft to a ram flow that is provided from outside ambient air;
a maintenance system including a processor;
a controller in informational communication with the sensor and with the maintenance system; and a fouling indicator in informational communication with the maintenance system;

wherein the maintenance system is programmed with a correlation of heat exchanger fouling to the operating variable, wherein the operating variable is chosen from inlet temperatures of input streams into the heat exchanger and outlet temperatures of output streams out of the heat exchanger, heat exchanger pressure drop, overall heat transfer coefficient value, speed of rotation of the air conditioning machine that includes the heat exchanger, and combinations thereof, and wherein the correlation comprises a mathematical model that uses heat exchanger effectiveness to relate heat exchanger fouling to the heat exchanger effectiveness.

* * * * *